US010638996B2

(12) United States Patent
Boll et al.

(10) Patent No.: US 10,638,996 B2
(45) **Date of Patent: *May 5, 2020**

(54) SYSTEM AND METHOD FOR INCREASING THE ACCURACY OF A MEDICAL IMAGING DEVICE

(71) Applicant: 3Shape A/S, Copenhagen K (DK)

(72) Inventors: Morten Boll, Espergærde (DK); Thomas Sangild Sørensen, Aarhus C (DK); Jens Peter Holme, Copenhagen S (DK); Sami Brandt, Malmö (SE); Henrik Öjelund, Kgs. Lyngby (DK)

(73) Assignee: 3Shape A/S, Kobenhavn K (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/420,338

(22) Filed: May 23, 2019

(65) Prior Publication Data

US 2020/0046308 A1 Feb. 13, 2020

Related U.S. Application Data

(63) Continuation of application No. 15/555,502, filed as application No. PCT/EP2016/054660 on Mar. 4, 2016, now Pat. No. 10,335,108.

(30) Foreign Application Priority Data

Mar. 4, 2015 (DK) ................................. 201570121

(51) Int. Cl.
*A61B 5/05* (2006.01)
*G06K 9/00* (2006.01)
(Continued)

(52) U.S. Cl.
CPC ............ *A61B 6/5229* (2013.01); *A61B 6/032* (2013.01); *A61B 6/0492* (2013.01);
(Continued)

(58) Field of Classification Search
USPC ................ 382/100, 103, 106–107, 128–134, 382/154–155, 162, 168, 173, 181, 189,
(Continued)

(56) References Cited

U.S. PATENT DOCUMENTS 5,023,894 A 6/1991 Yamashita et al.
5,954,647 A 9/1999 Bova et al.
(Continued)

FOREIGN PATENT DOCUMENTS

DE 10 2013 213 761 1/2015
WO 2011149182 12/2011

OTHER PUBLICATIONS

International Search Report (PCT/ISA/210) dated Jun. 21, 2016, by the Japanese Patent Office as the International Searching Authority for International Application No. PCT/EP2016/054660 (3 pages).
(Continued)

*Primary Examiner* — Seyed H Azarian
(74) *Attorney, Agent, or Firm* — Buchanan Ingersoll & Rooney PC

(57) ABSTRACT

A method for improving the accuracy of a digital medical model of a part of a patient, the method includes obtaining a set of at least 2 medical images of the patient, where an element comprising a predefined geometry and/or predefined information was attached to the patient during the recording of the medical images; obtaining at least 2 tracking images taken with at least one camera having a known positional relationship relative to the medical imaging device, said tracking images depicting at least part of the element; determining any movement of the element between acquisition of the at least 2 tracking images; and generating the digital medical model from the acquired medical images, wherein the determined movement of the element is used to
(Continued)

10
15
1
11
12
13 compensate for any movement of the patient between the acquisition of the medical images.

26 Claims, 4 Drawing Sheets

(51) Int. Cl.

| | |
|---|---|
| ***A61B 6/00*** | (2006.01) |
| ***H04N 5/247*** | (2006.01) |
| ***G06T 7/20*** | (2017.01) |
| ***G06T 7/00*** | (2017.01) |
| ***G16H 50/50*** | (2018.01) |
| ***A61B 6/04*** | (2006.01) |
| ***A61B 6/03*** | (2006.01) |
| ***G06T 7/70*** | (2017.01) |

(52) U.S. Cl.

CPC ............ *A61B 6/4085* (2013.01); *A61B 6/501* (2013.01); *A61B 6/5264* (2013.01); *G06T 7/0014* (2013.01); *G06T 7/20* (2013.01); *G06T 7/70* (2017.01); *G16H 50/50* (2018.01); *H04N 5/247* (2013.01); *G06T 2207/10081* (2013.01); *G06T 2207/30204* (2013.01)

(58) Field of Classification Search

USPC ....... 382/199, 219, 224, 232, 254, 274, 276, 382/286–291, 305, 312; 1/1; 348/65; 600/424, 426; 378/4, 21, 63

See application file for complete search history.

(56) References Cited

U.S. PATENT DOCUMENTS

| | | | | |
|---|---|---|---|---|
| 2003/0215051 | A1 | 11/2003 | Suzuki | |
| 2004/0122311 | A1 | 6/2004 | Cosman | |
| 2011/0123081 | A1 | 5/2011 | Sebok et al. | |
| 2012/0123251 | A1* | 5/2012 | Erbel | A61B 6/025 600/424 |
| 2013/0093866 | A1* | 4/2013 | Ohlhues | A61B 5/055 348/65 |
| 2013/0249907 | A1 | 9/2013 | Humphries et al. | |
| 2014/0107390 | A1 | 4/2014 | Brown | |
| 2014/0120493 | A1 | 5/2014 | Levin | |
| 2015/0243025 | A1* | 8/2015 | Berlinger | A61B 6/025 382/131 |
| 2016/0166226 | A1* | 6/2016 | Abkai | A61B 6/032 378/63 |
| 2017/0106208 | A1* | 4/2017 | Gauthier | A61N 5/1037 |

OTHER PUBLICATIONS

Written Opinion (PCT/ISA/237) dated Jun. 21, 2016, by the Japanese Patent Office as the international Searching Authority for International Application No. PCT/EP2016/054660 (6 pages).

* cited by examiner

501b – Tacking image camera(s)
501a – Medical imaging device
500 - system
502 - computer device
503 – micro processor
504 - computer readable medium
505 - visual display unit
506 - computer keyboard
507 - computer mouse
508 – transmission unit

SYSTEM AND METHOD FOR INCREASING THE ACCURACY OF A MEDICAL IMAGING DEVICE

CROSS REFERENCE TO RELATED APPLICATIONS

The present application is a continuation of U.S. application Ser. No. 15/555,502, which was filed on Sep. 2, 2017, which is a national stage application of PCT/EP2016/054660, filed on Mar. 4, 2016, and which claims the priority of Danish patent application number PA 2015 70121, filed on Mar. 4, 2015. The contents of U.S. application Ser. No. 15/555,502; PCT/EP2016/054660; and Danish patent application number PA 2015 70121 are all incorporated herein by reference.

FIELD OF THE INVENTION

This invention generally relates to a system and method for increasing the accuracy of a medical imaging system. More particularly, the invention relates to the tracking of patient movements during image acquisition in a medical imaging device, in particular in Cone Beam Computed Tomography (CBCT) scanners.

BACKGROUND OF THE INVENTION

Computed tomography, particularly x-ray computed tomography (CT), is a widely used volumetric imaging principle. In general terms, a radiation source and a radiation-sensitive image sensor are arranged on a line, with the subject of the examination positioned in between. The subject attenuates the radiation. The source-detector arrangement is typically moved into several positions, often on a circle or segment thereof, around the subject of the examination, and images are taken at every position. The spatial, volumetric distribution of the attenuation coefficient within the subject can then be reconstructed from all images, for example using the filtered back projection algorithm, generating a 3D digital model of the subject. Often, the image sensor is a 2D sensor, such as in cone beam computed tomography (CBCT). In medicine, x-ray CT scanners are valuable non-invasive diagnostic devices.

One of the major concerns related to the use of CT scanners in medicine is radiation dose. Accordingly, a large body of research has focused on volumetric reconstruction algorithms that exploit the image data in an optimal way, allowing fewer images to be taken, or a lower dose per image, for a given quality of the reconstruction. While filtered back projection is a direct algorithm, many refined algorithms are iterative ones. Because the volumetric reconstruction problem is ill-posed, various regularization approaches have been suggested, e.g., total variation. Maximum-likelihood estimation has also been proposed, for example with a prior based on material assumptions. Several proposed reconstruction algorithms contain some of the above elements, or all of them.

Another way to lower the needed dose in a CBCT system is to make sure the patient does not move during image acquisition. This is because for a given needed accuracy, the signal-to-noise ratio will be greater when the patient does not move. Also, when the patient moves, motion artifacts such as for example streaks and aliasing may deteriorate the image quality. Therefore, in general, the image quality will be better when patient movement is kept to a minimum.

In prior art CBCT systems, various forms of head fixation devices have been employed to keep the patient fixated during the x-ray recording. These systems all have the goal of minimizing effects from motion blur and patient movement, thereby achieving a higher accuracy of the final images. However, all these systems have the disadvantage that it may be uncomfortable for the patient to be fixated for the duration of the scan, in particular for patients that may suffer from claustrophobia. It therefore remains a problem to achieve a high accuracy of CBCT images without having to fixate the patient.

In general, in any image acquisition technique wherein there is the potential that the target object and imaging device may move relatively to each other it will be possible to achieve a better image quality in a system where it is possible to correct for this unwanted movement.

SUMMARY OF THE INVENTION

In one aspect there is disclosed a method for improving the accuracy of a digital medical model of a part of a patient, the digital medical model comprising at least 2 medical images recorded with a medical imaging device, the method comprising:

- obtaining a set of at least 2 medical images of the patient, where an element comprising a predefined geometry and/or predefined information was attached to the patient during the recording of the medical images;
- obtaining at least 2 tracking images taken with at least one camera having a known positional relationship relative to the medical imaging device, said tracking images depicting at least part of the element;
- determining any movement of the element between acquisition of the at least 2 tracking images; and
- generating the digital medical model from the acquired medical images, wherein the determined movement of the element is used to compensate for any movement of the patient between the acquisition of the medical images.

Accordingly, it is thus possible to correct any unwanted movement the patient makes during acquisition of the medical images when generating the digital medical model. The digital medical model may be for example a 3D model of parts of a patient's head taken with a cone beam computed tomography (CBCT) scanner, but may in general be any medical image or model taken over time, that requires a high accuracy. For example, the digital medical model may also be a 2D medical model such as a panoramic x-ray image or cephalometric x-ray image.

In some embodiments, the predefined information of the element comprises at least one fiducial marker, such as a plurality of fiducial markers in a predefined pattern, size, shape and/or colour.

When the placement, size, shape and/or colour of the fiducial markers are already known with very high accuracy before any images are taken, it is possible to determine with very high accuracy the movement of the element between images.

In some embodiments, compensating for any movement of the patient between the acquisition of the medical images comprises:

- associating a time stamp with each of the medical images, and each of the tracking images;
- determining the position and orientation of the element at each time stamp and determining therefrom the movement of the element during medical image acquisition;

adjusting the position of each pixel or voxel of the acquired medical image with an amount corresponding to the movement of the element.

In this way, it is possible to relate the movement of the element to the movement of the region of interest (ROI) on the patient, and adjust each of the medical images to account for any movement of the patient during an exposure of the medical imaging device. Therefore, when generating the digital medical model, instead of using medical images where the patient might have moved between images, the digital medical model can be generated with images corrected to simulate the situation where the patient has been still during the entire procedure.

In some embodiments, compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition;

generating the digital medical model from the acquired medical images, wherein the generating of the digital medical model movement of the element is accomplished by iteratively adjusting the digital medical model to account for the movement of the element during medical image acquisition.

Iteratively adjusting the digital medical model in this context may for example mean that a first estimate of the digital medical model is made using a computer device, using the acquired medical images before any adjustment due to the determined movement of the element. Then the determined movement of the element for each medical image can be applied to the digital medical model to iteratively improve the fit of the medical images to account for the movement of the element. So in this case, rather than adjusting the position of each voxel or pixel in the medical images and subsequently generating the digital medical model, the digital medical model is generated first, and then iteratively improved by using the adjusted position and orientation of the element and thereby the adjusted position and orientation of the image sensor relative to the patient.

In some embodiments, the tracking images and the medical images are time stamped using the same clock.

In order to correlate the movement of the patient with the medical imaging data, it is necessary to be able to map the movement of the element in time with the recording of the medical data. In principle, the cameras recording the element and the medical imaging sensor could be run using two separate processors with each their own clock. However, in this case, the two clocks would have to be synchronized in order to be able to map exactly the movement of the patient with the medical imaging data. A simpler solution is to have both the cameras and the medical imaging device run using the same clock. This can be accomplished for example by running the cameras and the medical imaging device from the same computer processor. The computer processor may be a stand-alone desktop or laptop computer or any other type of computer means, or it may be integrated in the scanner.

In some embodiments, determining the position and orientation of the element at each time stamp comprises:

recognizing a plurality of the individual fiducial markers in each tracking image;

obtaining a digital representation in a database of the known predefined pattern and/or shape of the fiducial markers;

recognizing the pattern of the fiducial markers in each image to achieve a best fit to the known predefined pattern of the fiducial markers on the element from each tracking image.

In order to determine the orientation and position of the element, mathematical optimization algorithms can be used. For example, if the fiducial markers are in the form of dots of a known size, the algorithms can be used to detect where there are dots and what size they have. The method used may for example be principal component analysis (PCA), although other methods are also possible and known to the person skilled in the art.

Since the fiducial markers have a known size, shape and/or predefined pattern on the element, once the size, shape and position of each found dot is determined, a mask comprising the known predefined pattern of the fiducial markers can by loaded from a database, be overlayed on the tracking image, and the fit of the tracking image to the mask can be determined, thereby finding the orientation and position of the element.

In some embodiments there may be more than one camera, such as two cameras or three cameras for recording the movement of the element. The reason for this, is that if only one camera is used, it is difficult to unambiguously determine how far away from the camera the fiducial marker is. If two cameras are used, it is difficult to unambiguously determine the position of the element in a direction that is parallel to a line connecting the two cameras. If, on the other hand, three cameras are used, possibly but not necessarily, placed for example at the points of an equilateral triangle, the position of the element in all three dimensions can be unambiguously determined.

Determining the position and orientation of the element using three cameras, can be accomplished for example by having the images from the three cameras time stamped so that at each time t, there are three images taken of the element, recognizing the fiducial markers in each image, determining a best fit to the known predefined pattern of the fiducial markers on the element in each image, determining the position and orientation of the element in each of the three images of the element at each time stamp, and computing a weighted average of the position and orientation of the element from the three images. In some embodiments, determining the position and orientation of the element at each time stamp comprises:

recognizing a plurality of the individual fiducial markers in each tracking image;

using classification of the indices of the fiducial markers; and matching the known pattern of the fiducial markers on the element to the pattern of the fiducial markers on the tracking image using the classification of the indices of the fiducial markers.

Matching the known pattern of the fiducial markers may for example be accomplished using a computer device, where the tracking images are loaded, and the fiducial markers are recognized and/or segmented in the tracking images. Then, the position of the fiducial markers in the tracking image are indexed, and the index of the fiducial markers in the tracking image are compared to the known index of the fiducial markers on the element. Since the distance between the fiducial markers on the element is known, the distances between the fiducial markers in the tracking images can be compared to the known distances, and known mathematical algorithms can be used to determine the position and rotation of the element in the tracking images.

In some embodiments, the camera position and rotation of each camera is calibrated or determined;

- the intrinsic parameters such as the focal length, skew, principal point and lens distortion are calibrated or determined for each camera;
- the tracking images from the three cameras are acquired simultaneously such that at each time t, there are three images taken of the element;
- the fiducial markers are recognized in each tracking image and the position of each fiducial marker is determined directly in the camera co-ordinate frame;
- the position and/or orientation of the element from the three images is determined using a cost function to minimise the difference in the determined position of the fiducial markers in each of the tracking images.

Since extrinsic parameters of the cameras are known (i.e. the position and rotation of the cameras with relation to the medical imaging device), and the fiducial markers are recognized in each image and the position of the fiducial markers are determined directly in the co-ordinate frame of the camera, the determination of the position and rotation of the element relative to the medical imaging device will be more accurate.

In some embodiments, the element is attached to a headband, which can be placed on the patient's head. It is an advantage if the headband is adjustable, since it should be possible to securely attach the headband to patients with different head sizes such as children and adults, without any risk of the headband moving during the exposure time.

The element may have only one fiducial marker, but preferably should have a plurality of fiducial markers on its surface, for example in the form of dots or circles. There may be any number of fiducial markers, for example more than 10, more than 100, more than 200 or more than 400 dots. Preferably there should be enough dots to make it simple to find the position and size of the dots, but not so many that it would take too much processing time.

The adjustment of the medical image may take place substantially in real time during acquisition of the medical image, or it may be done in post-processing. The advantage of doing the adjustments during acquisition is that it is possible to follow the final result of the image as it is being taken. However, this requires a substantial amount of processing power, so that it may be prohibitively expensive. Conversely, if the adjustment is not done in real time, there is less need for high processing power, since the processing can take longer than the time taken to acquire the medical images.

In some embodiments, there are asymmetrical features on the element or the element itself is asymmetrical. In principle, it is possible to determine the position and orientation of the element even if the fiducial markers are all placed in a completely symmetrical pattern. In this case, it would be assumed that the element has moved the shortest possible distance that is consistent with the pattern of the fiducial markers, between each time stamp. However, if the fiducial markers are placed asymmetrically, or if the element itself is asymmetrical, there is no ambiguity in when overlaying the mask of the known predefined pattern with the image of the element.

In some embodiments, generating the digital medical model is done in real time on a computer device while the medical images are being acquired. This has the advantage that the digital medical model can be visualized in real time. However, generating the digital medical model can in some situations, for example when the digital medical model is a 3D CBCT model, require substantial computer processing power. Therefore, it can often be the case that the digital medical model is only generated after all the medical images have been acquired.

The inventive concept of this specification can be used advantageously in any medical imaging device where it is important that the patient is still during imaging, such as standard x-ray, magnetic resonance imaging, positron emission tomography, etc. However, it is particularly useful in CBCT systems where it is very important to get a very high accuracy of the scan.

In CBCT systems, typical accuracy is in the range 75-350 at the moment, so the accuracy of position determination of the element should be on the order of the accuracy of the system. Therefore the accuracy of the determination of the position and orientation of the element should be at least 400 microns, such as 200 microns, less than 100 microns, less than 50 microns, less than 20 microns or less than 5 microns.

In another aspect there is disclosed a method for improving the accuracy of a digital medical model of a patient, the digital medical model being computed based on images recorded with a medical imaging device, the method comprising:

- obtaining a first tracking image taken with at least one camera having a known positional relationship relative to the medical imaging device, said tracking image depicting at least part of an element comprising a predefined geometry and/or predefined information;
- obtaining a first medical image of the patient, where an element comprising a predefined geometry and/or predefined information was attached to the patient during the recording of the medical image;
- obtaining at second tracking image taken with the at least one camera having a, said tracking image depicting at least part of the element;
- determining any movement of the element between acquisition of the 2 tracking images; and
- generating the digital medical model wherein the determined movement of the element is used to compensate for any movement of the patient relative to the medical imaging device during the acquisition of the medical image.

Accordingly, it is thus possible to correct any unwanted movement of the patient relative to the medical imaging device during the acquisition of each medical image. This may be relevant if the exposure time of each medical image is longer than the exposure time of each tracking image. For example, in an x-ray system, each medical image taken may require an exposure time on the order of tenths of a second, whereas the tracking images could have a needed exposure time of only hundredths of a second. In this case, when each x-ray image exposure time is longer than the tracking image exposure time, a plurality of tracking images can be taken during the acquisition of each medical image. Therefore, in these situations the digital medical model may be a single 2D image, such as a single exposure x-ray image. This method is of course not limited to x-ray imaging devices, but any medical imaging device in which the exposure time of the medical imaging device is longer than the exposure time of the tracking images.

The embodiments described above with respect to the first aspect of the invention, may also be used in connection with this aspect of the invention.

In another aspect there is disclosed a medical imaging system comprising:

- a radiation source emitting a radiation beam;
- a radiation sensor for detecting incident radiation from the radiation beam on a sensor area;

an element attachable to a patient, the element comprising a number of fiducial markers in a predefined pattern, size, shape and/or colour;

at least one camera configured to take tracking images of the element during the acquisition of medical images taken using the radiation source and radiation sensor; and computer means for determining a movement based on the tracking images, and for adjusting the medical images acquired using the radiation sensor to compensate for the movement.

In some embodiments, the element is attached to an adjustable headband. In this way the element can be made to fit patient's with different head sizes, such as both adults and children.

In some embodiments, the fiducial markers are in the form of circular dots. Dots or circles are simple geometrical features, that are easily recognized by computer algorithms.

In some embodiments, the system may include a mouthpiece for helping the patient stay still during the exposure. The mouthpiece may be in the form of a plate attached to the medical imaging device, and configured to allow the patient to bite onto the plate.

The element in this specification can be made from any material such as plastic, glass, metal or the like. It is, however important that the element is made out of a material that is substantially rigid, so that the known pattern of fiducial markers will not be distorted over time.

In some embodiments, the element is made of coated glass, and the fiducial markers are printed on the surface of the glass. This material is both rigid, and it is relatively simple to etch or print fiducial markers on the surface of the glass with high accuracy.

In the context of this specification, the term element should be understood to mean any device that can be attached to the patient for the purpose of tracking and determining their movement, and should therefore not be confined to mean only a flat rectangular piece of metal or plastic. In principle, the form of the element could be for example circular, semi-circular, pyramidal, triangular, or any other shape. The element could even be a complex three dimensional shape, where the shape of the element itself is used as the fiducial markers.

In the context of this specification, it should be understood that although there may be a reference to a medical image of a patient, this should be understood in the broadest sense, so that this also means that the medical image can be of only a part of the patient, such as the head of the patient, a jaw of the patient or any other part of the patient.

EMBODIMENTS

1. A method for improving the accuracy of a digital medical model of a part of a patient, the medical model comprising at least 2 medical images recorded with a medical imaging device, the method comprising:

obtaining a set of at least 2 medical images of the patient, where an element comprising a predefined geometry and/or predefined information was attached to the patient during the recording of the medical images;

obtaining at least 2 tracking images taken with at least one camera having a known positional relationship relative to the medical imaging device, said tracking images depicting at least part of the element;

determining any movement of the element between acquisition of the at least 2 tracking images; and generating the digital medical model from the acquired medical images, wherein the determined movement of the element is used to compensate for any movement of the patient between the acquisition of the medical images.

2. The method according to embodiment 1, wherein the predefined information of the element comprises at least one fiducial marker, such as a plurality of fiducial markers in a predefined pattern, size, shape and/or colour.

3. The method according to embodiment 1, wherein the predefined information of the element comprises the geometric shape of the element.

4. The method according to any one or more of the preceding embodiments, wherein compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition;

adjusting the position of each pixel or voxel of the acquired medical image with an amount corresponding to the movement of the element.

5. The method according to any one or more of the preceding embodiments, wherein compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition;

generating the digital medical model from the acquired medical images, wherein the generating of the digital medical model comprises iteratively adjusting the digital medical model to account for the movement of the element during medical image acquisition.

6. The method according to any one or more of the preceding embodiments, wherein the coordinate system used in determining the position and orientation of the element can be fixed arbitrarily.

7. The method according to any one or more of the preceding embodiments, wherein the tracking images taken and the medical images are time stamped using the same clock.

8. The method according to any one or more of embodiments 4-7, wherein determining the position and orientation of the element at each time stamp comprises:

recognizing a plurality of the individual fiducial markers in each tracking image;

obtaining a digital representation in a database of the known predefined pattern and/or shape of the fiducial markers;

recognizing the pattern of the fiducial markers in each image to achieve a best fit to the known predefined pattern of the fiducial markers on the element from each tracking image.

9. The method according to any one or more of embodiments 4-7, wherein determining the position and orientation of the element at each time stamp comprises:

recognizing a plurality of the individual fiducial markers in each tracking image;

using a classification of the indices of the fiducial markers; and matching the known pattern of the fiducial markers on the element to the pattern of the fiducial markers on the tracking image using the classification of the indices of the fiducial markers.

10. The method according to any one or more of the preceding embodiments, wherein recognizing the fiducial markers comprises performing principal component analysis on the tracking images in order to segment the fiducial markers.

11. The method according to any one or more of the preceding embodiments wherein there are three cameras for recording the movement of the element, such as three cameras placed at the points of an equilateral triangle.

12. The method according to embodiment 11 wherein:

the tracking images from the three cameras are acquired simultaneously such that at each time t, there are three images taken of the element;

the fiducial markers are recognized in each image;

the pattern of the fiducial markers is recognized in each tracking image to achieve a best fit to the known predefined pattern of the fiducial markers on the element from each tracking image;

the position and orientation of the element in each of the three tracking images each time t is determined; and a weighted average of the position and orientation of the element from the three images is used to determine the best fit for the position and orientation of the element at each time t.

13. The method according to any one or more of embodiments 11-12 wherein:

the camera position and rotation of each camera is calibrated or determined;

the intrinsic parameters such as the focal length, skew, principal point and lens distortion are calibrated or determined for each camera;

the tracking images from the three cameras are acquired simultaneously such that at each time t, there are three images taken of the element;

the fiducial markers are recognized in each tracking image and the position of each fiducial marker is determined directly in the camera co-ordinate frame;

the position and/or orientation of the element from the three images is determined using a cost function to minimise the difference in the determined position of the fiducial markers in each of the tracking images.

14. The method according to any of one or more of the preceding embodiments, wherein the digital medical model is generated in real time.

15. The method according to any one or more of the preceding embodiments, wherein the medical imaging device is a cone beam computed tomography device.

16. A method for improving the accuracy of a digital medical model of a patient, the digital medical model being computed based on images recorded with a medical imaging device, the method comprising:

obtaining a first tracking image taken with at least one camera having a known positional relationship relative to the medical imaging device, said tracking image depicting at least part of an element comprising a predefined geometry and/or predefined information;

obtaining a first medical image of the patient, where an element comprising a predefined geometry and/or predefined information was attached to the patient during the recording of the medical image;

obtaining at second tracking image taken with the at least one camera having a, said tracking image depicting at least part of the element;

determining any movement of the element between acquisition of the 2 tracking images; and generating the digital medical model wherein the determined movement of the element is used to compensate for any movement of the patient relative to the medical imaging device during the acquisition of the medical image 17. The method according to embodiment 16, wherein the predefined information of the element comprises at least one fiducial marker, such as a plurality of fiducial markers in a predefined pattern, size, shape and/or colour.

18. The method according to embodiment 16, wherein the predefined information of the element comprises the geometric shape of the element.

19. The method according to any one or more of embodiments 16-18, wherein compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition;

adjusting the position of each pixel or voxel of the acquired medical image with an amount corresponding to the movement of the element.

20. The method according to any one or more of embodiments 16-18, wherein compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition;

generating the digital medical model from the acquired medical images, wherein the generating of the digital medical model comprises iteratively adjusting the digital medical model to account for the movement of the element during medical image acquisition.

21. The method according to any one or more of embodiments 16-20, wherein the coordinate system used in determining the position and orientation of the element can be fixed arbitrarily.

22. The method according to any one or more of embodiments 16-20, wherein the tracking images taken and the medical images are time stamped using the same clock.

23. The method according to any one or more of embodiments 19-22, wherein determining the position and orientation of the element at each time stamp comprises:

recognizing a plurality of the individual fiducial markers in each tracking image;

obtaining a digital representation in a database of the known predefined pattern and/or shape of the fiducial markers;

recognizing the pattern of the fiducial markers in each image to achieve a best fit to the known predefined pattern of the fiducial markers on the element from each tracking image 24. The method according to any one or more of embodiments 19-22, wherein determining the position and orientation of the element at each time stamp comprises:

recognizing a plurality of the individual fiducial markers in each tracking image;

using a classification of the indices of the fiducial markers; and matching the known pattern of the fiducial markers on the element to the pattern of the fiducial markers on the tracking image using the classification of the indices of the fiducial markers.

25. The method according to any one or more of embodiments 19-24, wherein recognizing the fiducial markers comprises performing principal component analysis on the tracking images in order to segment the fiducial markers.

26. The method according to any one or more of embodiments 19-24 wherein there are three cameras for recording the movement of the element, such as three cameras placed at the points of an equilateral triangle.

27. The method according to embodiment 26 wherein:
   - the tracking images from the three cameras are acquired simultaneously such that at each time t, there are three images taken of the element;
   - the fiducial markers are recognized in each image;
   - the pattern of the fiducial markers is recognized in each tracking image to achieve a best fit to the known predefined pattern of the fiducial markers on the element from each tracking image;
   - the position and orientation of the element in each of the three tracking images each time t is determined; and
   - a weighted average of the position and orientation of the element from the three images is used to determine the best fit for the position and orientation of the element at each time t.

28. The method according to any one or more of embodiments 26-27 wherein:
   - the camera position and rotation of each camera is calibrated or determined;
   - the intrinsic parameters such as the focal length, skew, principal point and lens distortion are calibrated or determined for each camera;
   - the tracking images from the three cameras are acquired simultaneously such that at each time t, there are three images taken of the element;
   - the fiducial markers are recognized in each tracking image and the position of each fiducial marker is determined directly in the camera co-ordinate frame;
   - the position and/or orientation of the element from the three images is determined using a cost function to minimise the difference in the determined position of the fiducial markers in each of the tracking images.

29. The method according to any one or more of embodiments 16-28, wherein the medical imaging device is a cone beam computed tomography device.

30. A medical imaging system comprising:
   - a radiation source emitting a radiation beam;
   - a radiation sensor for detecting incident radiation from the radiation beam on a sensor area;
   - an element attachable to a patient, the element comprising a number of fiducial markers in a predefined pattern, size, shape and/or colour;
   - at least one camera configured to take tracking images of the element during the acquisition of medical images taken using the radiation source and radiation sensor; and
   - computer means for determining a movement based on the tracking images, and for adjusting the medical images acquired using the radiation sensor to compensate for the movement.

BRIEF DESCRIPTION OF THE DRAWINGS

The above and/or additional objects, features and advantages of the present invention, will be further described by the following illustrative and non-limiting detailed description of embodiments of the present invention, with reference to the appended drawings, wherein.

DETAILED DESCRIPTION

Figure 1:
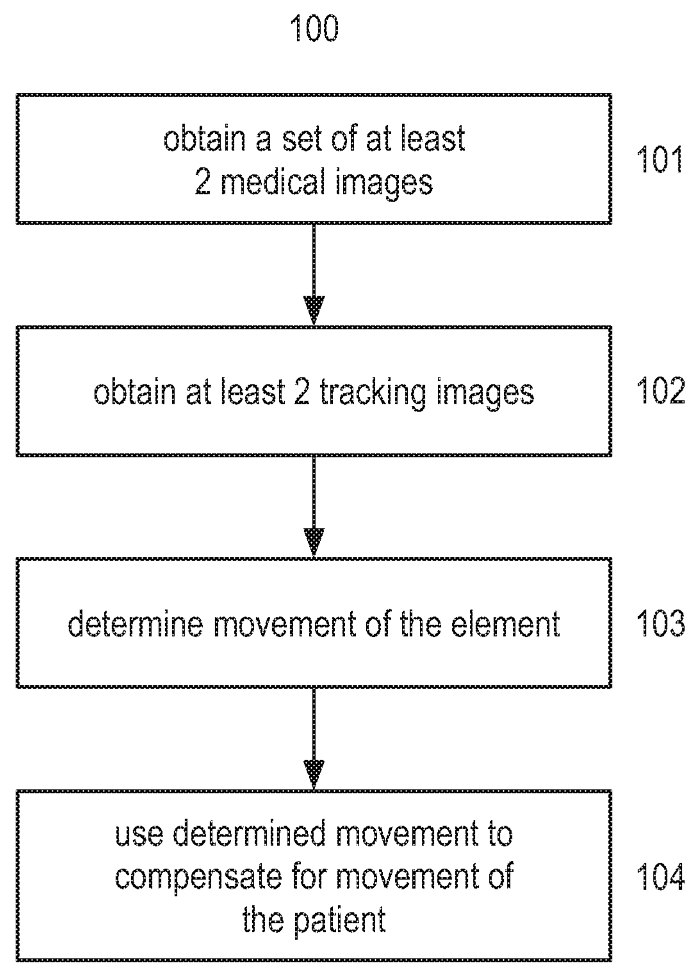
FIG. 1 shows a flow chart of a method according to an embodiment of this invention.

An embodiment of the method disclosed herein is shown in FIG. 1.

In step 101, a set of at least 2 medical images of the patient, are obtained. In step 102, at least 2 tracking images are obtained. The tracking images are images of an element that was attached to the patient during the taking of the medical images. The tracking images and the medical images can be related, because the tracking images and the medical images are time stamped. In step 103, any movement of the element between acquisition of the tracking images is determined using computer processing means. In step 104, the determined movement of the element is used to compensate for any movement of the patient between the acquisition of the medical images, and a digital medical model is generated using the adjusted medical images.

Figure 2:
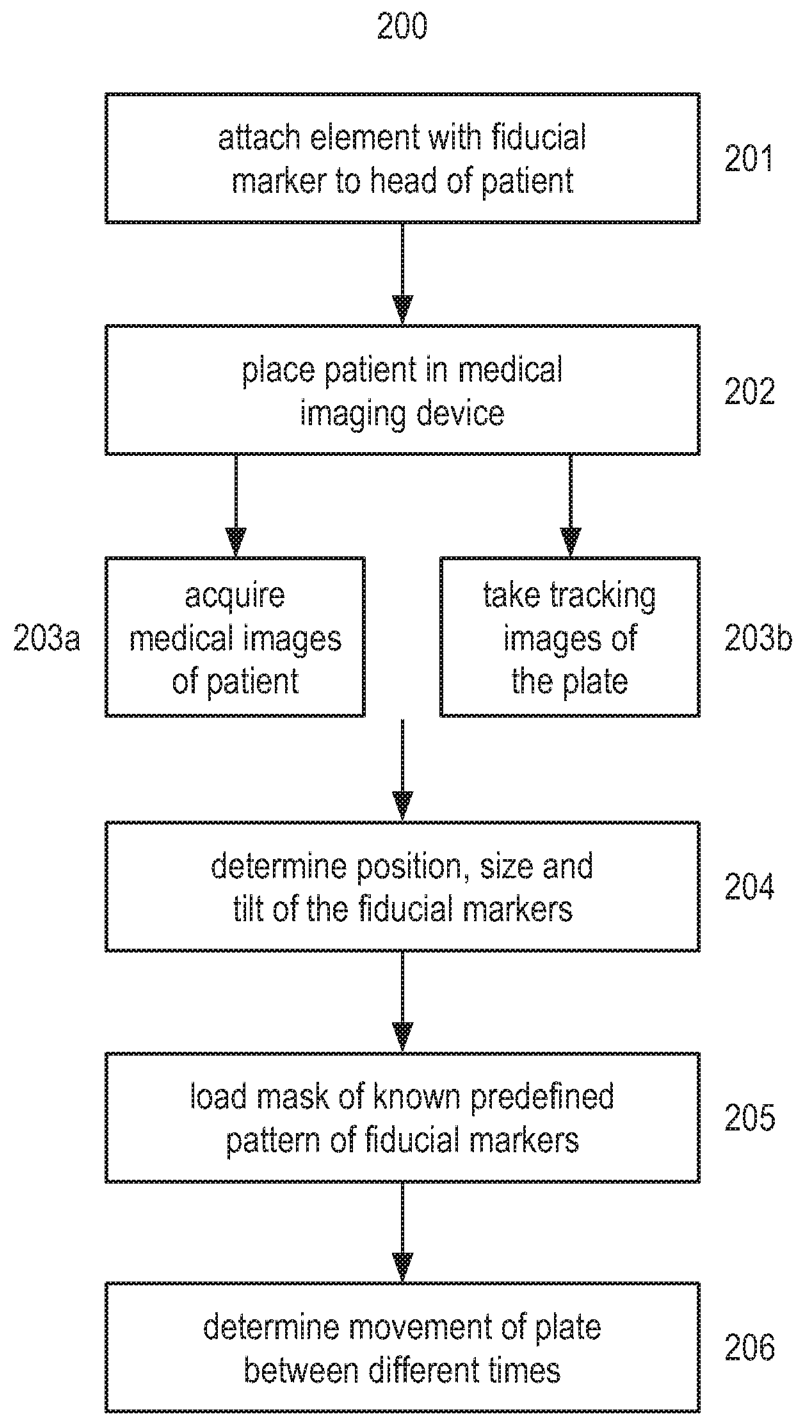
FIG. 2 shows a flow chart of a method according to another aspect of this invention.

FIG. 2 shows a flow chart representing an embodiment of the method disclosed herein. In step 201, an element, here in the form of a plate, with at least one fiducial marker is attached to the head of a patient. The fiducial markers may be any shape, for example a circle, triangle, ellipse, or any other geometrical shape. In step 202, the patient is placed in a medical imaging device, for example a CBCT scanner. In step 203*a*, the medical imaging device acquires medical images of the patient. Concurrently with step 203*a*, in step 203*b*, tracking images of the plate are taken using one or more cameras that are placed in a known spatial relationship with the medical imaging source and sensor. The cameras may be integrated into the medical imaging device, or they may be a separate system. In step 204, the position, size and tilt of the fiducial markers is determined. This can for example be done by using principal component analysis. If, for example the fiducial markers are in the form of circular dots, when there is an angle between a normal vector of the plate and a linear axis between the plate and the camera, the circular dots will look slightly deformed in the tracking image. In this case, principal component analysis can be used to determine whether what is observed in the image is a dot, and where the center of the dot is located. In step 205, a mask of the known predefined pattern of the fiducial markers is loaded from a database, and compared with the determined pattern of fiducial markers in each tracking image. This comparison can be done using any method known in the art. This allows the position and orientation of the plate to be determined. It may be advantageous to determine the orientation of the midpoint of the plate, since this will allow the highest accuracy. However, the position and orientation of any point on the plate may be used, for example the corner of the plate. If there is more than one camera, a tracking image from each camera will be taken at each time t. Each of these tracking images will then have a determined position and orientation of the plate at each time t. The position and orientation determined from each tracking image at time t may be slightly different because of the particular geometry of the situation, for example one camera may have a more acute angle towards the plate than another. The determined position and orientation from each tracking image at time t may then be combined into a single determined position and orientation. This combination can for example be done by performing a weighted average of the position and orientation measurement from each tracking image at time t.

The weighted average can for example be computed by starting with the found position and orientation of the element from one image, determining the difference between this starting position and the position and orientation of the element in each of the other two images, and iteratively adjusting the starting position and orientation of the element to an adjusted position and orientation, until the combined error or difference between the position and orientation of the element in each image and the adjusted position and orientation is minimized.

Alternatively, the starting position and orientation of the element could be a standard default position and orientation, and the difference between this standard position and orientation and the position and orientation determined in each of the three images can be computed. Then the starting position and orientation of the element can be iteratively adjusted until the combined error or difference between the position and orientation of the element in each image and the adjusted starting position is minimized. Therefore the accuracy of the determined position and orientation of the plate will be better when more than one camera is used.

An alternative approach to the comparison step 205 may be accomplished as follows. Instead of having a database containing a mask of the known predefined pattern of the fiducial pattern or markers, there may instead be a classification of the indices of each of the fiducial markers, as explained in relation to FIG. 3. In this way, the 3D position and orientation of the element is then found such that the classification indices of the known pattern is matched with the determined indices of the fiducial markers on the image sensor after projecting. Here it is important to note that the field of view of each camera, should be large enough to unambiguously determine which part of the element is in the image. In the case of more than one camera, there may be ambiguities as to the exact position and orientation of the element as determined from the tracking images taken with different cameras. In this case, a cost function may be used, so that the position and orientation determination is optimized using information from all cameras. In step 206, the movement of the plate between different times t is determined, and the determined movement of the plate is used to adjust the position and/or orientation of each pixel or voxel in a digital medical model. Since the positional relationship between the cameras and the medical imaging source and sensor is known, any movement of the plate can be directly translated into a corresponding movement of the patient, and this movement of the patient can be used to adjust the position and/or orientation of each pixel in the digital medical model of a part of the patient.

Figure 3:
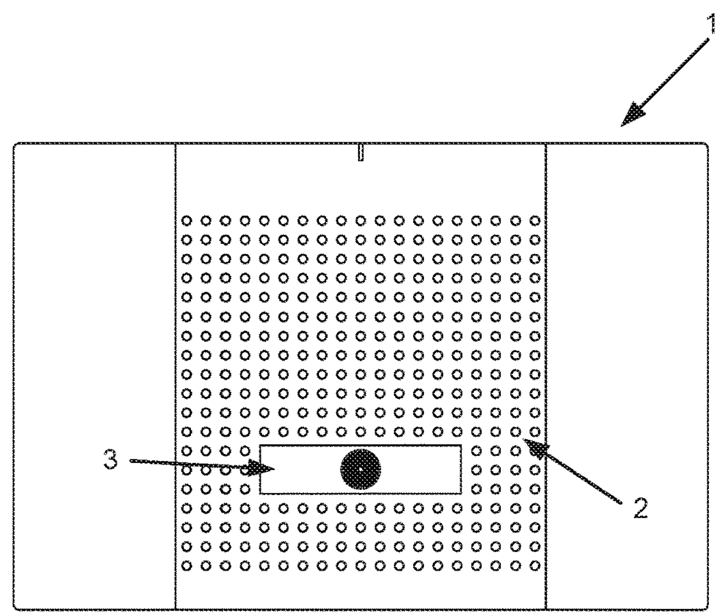
FIG. 3 shows an element according to an embodiment of this invention.

In FIG. 3, an element 1 according to embodiments of this disclosure is shown. The element has the form of a rectangular plate, made of a rigid material. The plate has a plurality of fiducial markers 2, in a predetermined pattern, layout or configuration. The pattern should be known to a very high degree of accuracy, so that matching subsequent tracking images taken of the plate, can be matched with a mask of the same pattern saved in a database. In CBCT systems today, typical accuracy is in the range 75-350 microns at the moment. Therefore, the accuracy of the known placement of each fiducial marker should at least be within this range in order to achieve a higher accuracy in the digital medical model. Of course, the higher the accuracy of the placement of the fiducial markers, the more the accuracy of the digital medical model will be improved.

Each fiducial marker may be classified using a classification index. For example, the fiducial marker closes to one corner could be defined as having the index (0,0), the next one in the same row could have the index (0,1) and in general the fiducial markers could have an index defined as (i,j), with l going from 0 to n, and j going from 0 to m. In this way, the fiducial markers will have a known classification index, which can then be compared to tracking images to match the actual pattern of the fiducial markers on the element to the fiducial markers in the tracking images.

The plate may also comprise an asymmetrical feature 3. This will make it easier for computer algorithms to unambiguously match the pattern from the database to the tracking images, and therefrom derive the actual position and orientation of the element in each tracking image. In the case where the fiducial markers are classified using a classification index, the asymmetrical feature will mean that it will be easier to make sure that each tracking camera has a view of the element wherein the position and orientation of the element in the field of view of the camera can more easily be unambiguously derived. That is, once the fiducial markers have been segmented in the tracking images, for example using PCA, they can be classified according to the classification index. If, on the other hand, the field of view of the tracking camera only covered an ambiguous subset of the fiducial markers, it would be impossible to unambiguously derive the position and orientation of the element in the tracking image.

The element may be made of any rigid material such as plastic, metal or glass. When using coated glass for the element, it is easy to print or etch the fiducial markers onto or into the surface of the element.

Although illustrated here as a rigid plate on which the fiducial markers are printed or etched, the element may also for example be a plate with holes, with lights placed underneath the holes, so that the position of the lights can be picked up by a sensor. The lights could for instance use infrared wavelengths, and the sensor could be an infrared sensor. Another option could be to have an active plate where lights are placed on the surface of the plate, and the position of these lights could be picked up by a sensor. For example, the light could be LED lights.

Figure 4:
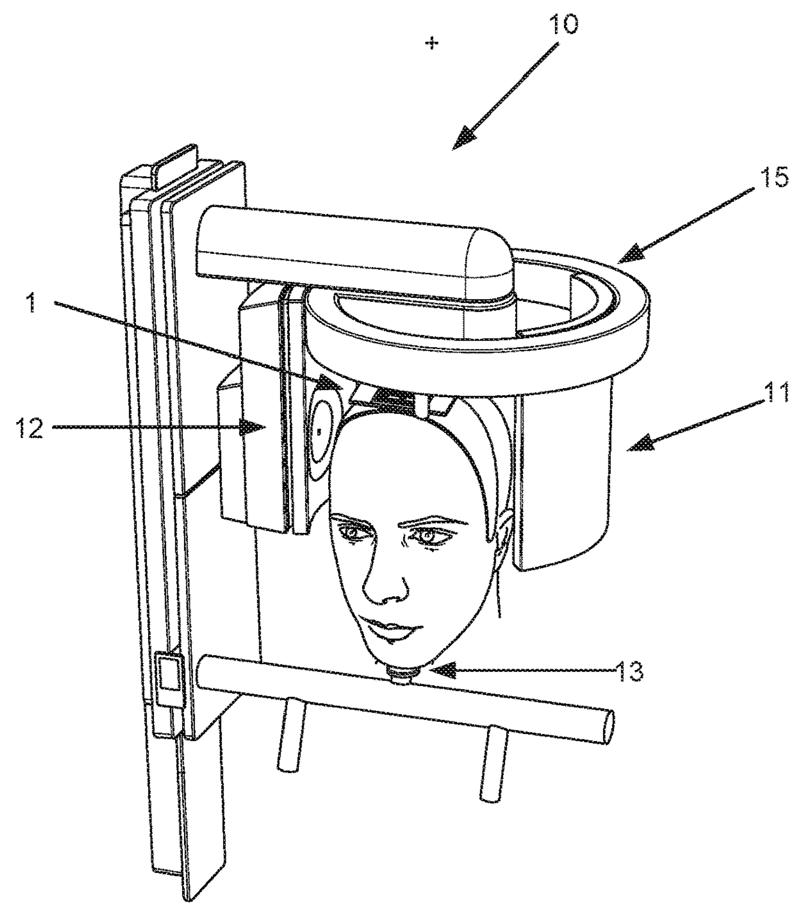
FIG. 4 shows a medical imaging system according to an embodiment of this invention.

Turning now to FIG. 4, a system according to an aspect of this invention is shown. The system comprises a medical imaging device in the form of a CBCT scanner 10, where the CBCT scanner comprises a sensor 11, and a radiation source 12. The sensor and/or the radiation source are able to turn substantially around a full circle around the patient's head. The system may also comprise a chin rest 13 for the patient to rest his/her chin. The system may also include a face scanner (not shown), the face scanner configured to record a 3D model of the patient's face. The system further comprises an element 1, here shown as a plate attachable to the patient's head. Also comprised in the system is one or more cameras, for example located inside the ring 15. The cameras should be mounted with a known geometrical relationship to the sensor 11 and radiation source 12. Often, this will be near or in the center of the ring 15, since the patient will usually be positioned underneath the center of the ring 15. The cameras are configured to be used to take tracking images of the element 1 simultaneously with the medical imaging device taking medical images.

Figure 5:
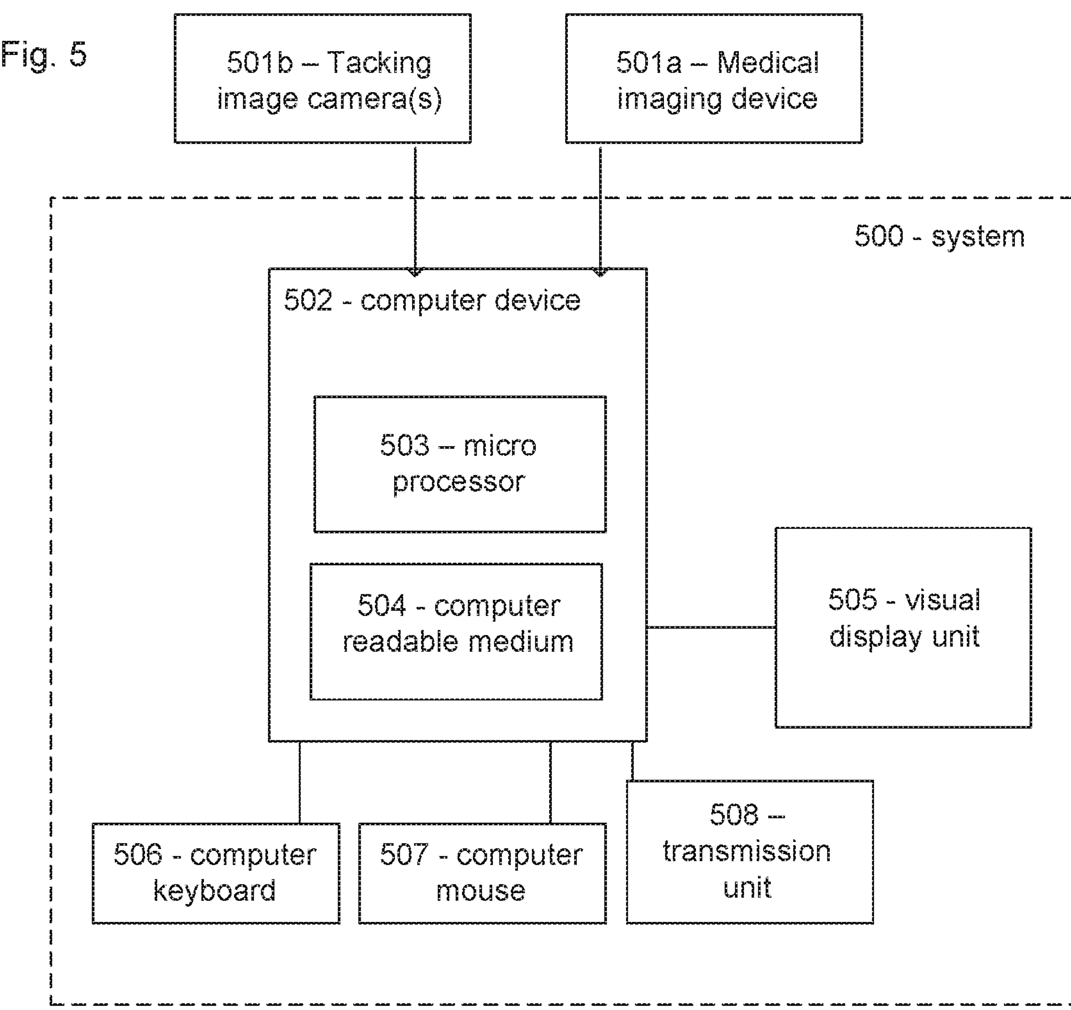
FIG. 5 shows a system according to an embodiment of this invention.

FIG. 5 shows a schematic of a system according to an embodiment of the invention. The system 500 comprises a computer device 502 comprising a computer readable medium 504 and a microprocessor 503. The system further comprises a visual display unit 505, a computer keyboard 506 and a computer mouse 507 for entering data and activating digital buttons visualized on the visual display unit 505. The visual display unit 505 can be a computer screen, or a tablet computer, or any other digital display unit.

The computer device 502 is capable of obtaining medical images recorded with one or more medical imaging devices 501*a* and tracking images recorded by one or more cameras 501*b*. The obtained medical images and tracking images can be stored in the computer readable medium 504 and provided to the processor 503. In some embodiments system 500 may be configured for allowing an operator to control the medical imaging device using the computer device 502. The controls may displayed digitally on the visual display unit 505, and the user may control the medical imaging device, as well as the tracking cameras using the computer keyboard 506 and computer mouse 507.

The system may comprise a unit 508 for transmitting the medical images, the tracking images and/or the digital medical model via the internet, for example to a cloud storage.

The medical imaging device 501*a* may be for example a CBCT unit located for example at a dentist.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

The term "obtaining" as used in this specification may refer to physically acquiring for example medical images using a medical imaging device, but it may also refer for example to loading into a computer an image or a digital representation previously acquired.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method for improving the accuracy of a digital medical model of a part of a patient, the medical model comprising at least two medical images recorded with a medical imaging device, the method comprising:

obtaining a set of at least two medical images of the patient, where an element comprising a predefined geometry or predefined information was in a stationary relationship with the patient during the recording of the medical images;

obtaining at least two tracking images taken with at least one camera having a known positional relationship relative to the medical imaging device, said tracking images depicting at least part of the element;

determining any movement of the element between acquisition of the at least two tracking images; and generating the digital medical model from the acquired medical images, wherein the determined movement of the element is used to compensate for any movement of the patient between the acquisition of the medical images;

wherein compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition;

generating the digital medical model from the acquired medical images, wherein the generating of the digital medical model comprises iteratively adjusting the digital medical model to account for the movement of the element during medical image acquisition;

wherein the predefined information of the element comprises at least one fiducial marker, such as a plurality of fiducial markers in a predefined pattern, size, shape or colour.

2. The method according to claim 1, wherein the predefined information of the element comprises the geometric shape of the element.

3. The method according to claim 1, wherein compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition;

adjusting the position of each pixel or voxel of the acquired medical image with an amount corresponding to the movement of the element.

4. The method according to claim 1, wherein the coordinate system used in determining the position and orientation of the element can be fixed arbitrarily.

5. The method according to claim 1, wherein the tracking images taken and the medical images are time stamped using the same clock.

6. A method for improving the accuracy of a digital medical model of a part of a patient, the medical model comprising at least two medical images recorded with a medical imaging device, the method comprising:

obtaining a set of at least two medical images of the patient, where an element comprising a predefined geometry or predefined information was in a stationary relationship with the patient during the recording of the medical images;

obtaining at least two tracking images taken with at least one camera having a known positional relationship relative to the medical imaging device, said tracking images depicting at least part of the element;

determining any movement of the element between acquisition of the at least two tracking images; and generating the digital medical model from the acquired medical images, wherein the determined movement of the element is used to compensate for any movement of the patient between the acquisition of the medical images;

wherein determining the position and orientation of the element at each time stamp comprises:

recognizing a plurality of the individual fiducial markers in each tracking image;

obtaining a digital representation in a database of the known predefined pattern or shape of the fiducial markers;

recognizing the pattern of the fiducial markers in each image to achieve a best fit to the known predefined pattern of the fiducial markers on the element from each tracking image;

wherein recognizing the fiducial markers comprises performing principal component analysis on the tracking images in order to segment the fiducial markers.

7. A method for improving the accuracy of a digital medical model of a part of a patient, the medical model comprising at least two medical images recorded with a medical imaging device, the method comprising:

obtaining a set of at least two medical images of the patient, where an element comprising a predefined geometry or predefined information was in a stationary relationship with the patient during the recording of the medical images;

obtaining at least two tracking images taken with at least one camera having a known positional relationship relative to the medical imaging device, said tracking images depicting at least part of the element;

determining any movement of the element between acquisition of the at least two tracking images; and generating the digital medical model from the acquired medical images, wherein the determined movement of the element is used to compensate for any movement of the patient between the acquisition of the medical images;

wherein determining the position and orientation of the element at each time stamp comprises:

recognizing a plurality of the individual fiducial markers in each tracking image;

using a classification of the indices of the fiducial markers; and matching the known pattern of the fiducial markers on the element to the pattern of the fiducial markers on the tracking image using the classification of the indices of the fiducial markers;

wherein recognizing the fiducial markers comprises performing principal component analysis on the tracking images in order to segment the fiducial markers.

8. The method according to claim 7, wherein there are three cameras for recording the movement of the element, such as three cameras placed at the points of an equilateral triangle.

9. The method according to claim 8, wherein:

the tracking images from the three cameras are acquired simultaneously such that at each time t, there are three images taken of the element;

the fiducial markers are recognized in each image;

the pattern of the fiducial markers is recognized in each tracking image to achieve a best fit to the known predefined pattern of the fiducial markers on the element from each tracking image;

the position and orientation of the element in each of the three tracking images each time t is determined; and a weighted average of the position and orientation of the element from the three images is used to determine the best fit for the position and orientation of the element at each time t.

10. The method according to claim 8, wherein:

the camera position and rotation of each camera is calibrated or determined;

the intrinsic parameters such as the focal length, skew, principal point and lens distortion are calibrated or determined for each camera;

the tracking images from the three cameras are acquired simultaneously such that at each time t, there are three images taken of the element;

the fiducial markers are recognized in each tracking image and the position of each fiducial marker is determined directly in the camera co-ordinate frame;

the position or orientation of the element from the three images is determined using a cost function to minimise the difference in the determined position of the fiducial markers in each of the tracking images.

11. The method according to claim 7, wherein the digital medical model is generated in real time.

12. The method according to claim 7, wherein the medical imaging device is a cone beam computed tomography device.

13. A method for improving the accuracy of a digital medical model of a patient, the digital medical model being computed based on images recorded with a medical imaging device, the method comprising:

obtaining a first tracking image taken with at least one camera having a known positional relationship relative to the medical imaging device, said tracking image depicting at least part of an element comprising a predefined geometry or predefined information;

obtaining a first medical image of the patient, where an element comprising a predefined geometry or predefined information was in a stationary relationship with the patient during the recording of the medical image;

obtaining at second tracking image taken with the at least one camera having a, said tracking image depicting at least part of the element;

determining any movement of the element between acquisition of the two tracking images; and generating the digital medical model wherein the determined movement of the element is used to compensate for any movement of the patient relative to the medical imaging device during the acquisition of the medical image;

wherein compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition;

generating the digital medical model from the acquired medical images, wherein the generating of the digital medical model comprises iteratively adjusting the digital medical model to account for the movement of the element during medical image acquisition;

wherein the predefined information of the element comprises at least one fiducial marker, such as a plurality of fiducial markers in a predefined pattern, size, shape or colour.

14. The method according to claim 13, wherein the predefined information of the element comprises the geometric shape of the element.

15. The method according to claim 13, wherein compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition;

adjusting the position of each pixel or voxel of the acquired medical image with an amount corresponding to the movement of the element.

16. The method according to claim 15, wherein determining the position and orientation of the element at each time stamp comprises:

recognizing a plurality of the individual fiducial markers in each tracking image;

obtaining a digital representation in a database of the known predefined pattern and/or shape of the fiducial markers;

recognizing the pattern of the fiducial markers in each image to achieve a best fit to the known predefined pattern of the fiducial markers on the element from each tracking image.

17. The method according to claim 15, wherein determining the position and orientation of the element at each time stamp comprises:

recognizing a plurality of the individual fiducial markers in each tracking image;

using a classification of the indices of the fiducial markers; and matching the known pattern of the fiducial markers on the element to the pattern of the fiducial markers on the tracking image using the classification of the indices of the fiducial markers.

18. The method according to claim 15, wherein recognizing the fiducial markers comprises performing principal component analysis on the tracking images in order to segment the fiducial markers.

19. The method according to claim 15, wherein there are three cameras for recording the movement of the element, such as three cameras placed at the points of an equilateral triangle.

20. The method according to claim 19, wherein:

the tracking images from the three cameras are acquired simultaneously such that at each time t, there are three images taken of the element;

the fiducial markers are recognized in each image;

the pattern of the fiducial markers is recognized in each tracking image to achieve a best fit to the known predefined pattern of the fiducial markers on the element from each tracking image;

the position and orientation of the element in each of the three tracking images each time t is determined; and a weighted average of the position and orientation of the element from the three images is used to determine the best fit for the position and orientation of the element at each time t.

21. The method according to claim 19, wherein:

the camera position and rotation of each camera is calibrated or determined;

the intrinsic parameters such as the focal length, skew, principal point and lens distortion are calibrated or determined for each camera;

the tracking images from the three cameras are acquired simultaneously such that at each time t, there are three images taken of the element;

the fiducial markers are recognized in each tracking image and the position of each fiducial marker is determined directly in the camera co-ordinate frame;

the position and/or orientation of the element from the three images is determined using a cost function to minimise the difference in the determined position of the fiducial markers in each of the tracking images.

22. The method according to claim 13, wherein compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition;

generating the digital medical model from the acquired medical images, wherein the generating of the digital medical model comprises iteratively adjusting the digital medical model to account for the movement of the element during medical image acquisition.

23. The method according to claim 13, wherein the coordinate system used in determining the position and orientation of the element can be fixed arbitrarily.

24. The method according to claim 13, wherein the tracking images taken and the medical images are time stamped using the same clock.

25. The method according to claim 13, wherein the medical imaging device is a cone beam computed tomography device.

26. A medical imaging system comprising:

a radiation source emitting a radiation beam;

a radiation sensor for detecting incident radiation from the radiation beam on a sensor area;

an element attachable to a patient, the element comprising a number of fiducial markers in a predefined pattern, size, shape or colour;

at least one camera configured to take at least two tracking images of the element during the acquisition of medical images taken using the radiation source and radiation sensor, wherein the tracking images depict at least part of the element; and computer means for determining a movement based on the tracking images, and for adjusting the medical images acquired using the radiation sensor to compensate for the movement;

wherein compensating for any movement of the patient between the acquisition of the medical images comprises:

associating a time stamp with each of the medical images, and each of the tracking images;

determining the position and orientation of the element at each time stamp and determining therefrom the movement of the element during medical image acquisition, and the element comprises a predefined geometry or predefined information in a stationary relationship with the patient during the recording of the medical images;

generating the digital medical model from the acquired medical images, wherein the generating of the digital medical model comprises iteratively adjusting the digital medical model to account for the movement of the element during medical image acquisition.

* * * * *